United States Patent [19]

van der Drift et al.

[11] 4,128,547
[45] Dec. 5, 1978

[54] 6-(D-α-AMINO-P-HYDROXY-PHENYLACETAMIDO)-PENICILLANIC ACID PREPARATION

[75] Inventors: Johannes K. van der Drift, Delft; Peter W. Henniger, Leiden; Gerard J. van Veen, Pijnacker, all of Netherlands

[73] Assignee: Gist-Brocades N.V., Delft, Netherlands

[21] Appl. No.: 854,821

[22] Filed: Nov. 25, 1977

[30] Foreign Application Priority Data

Oct. 31, 1977 [JP] Japan ................................ 52-130694
Sep. 6, 1977 [NL] Netherlands ........................ 7709812

[51] Int. Cl.² .................. C07D 499/12; C07D 499/04
[52] U.S. Cl. ................................................. 260/239.1
[58] Field of Search ...................................... 260/239.1

[56] References Cited

U.S. PATENT DOCUMENTS 3,946,003   3/1976   Cooper ............................ 260/243 C

*Primary Examiner*—Gerald A. Schwartz
*Attorney, Agent, or Firm*—Hammond & Littell

[57] ABSTRACT

A process for the preparation of 6-(D-α-amino-p-hydroxyphenylacetamido)-penicillanic acid or amoxicillin by reacting 6-aminopenicillanic acid with at least two equivalents of a silylating agent producing trimethylsilyl groups in an anhydrous, inert, water-insoluble organic solvent and reacting the resulting product at a temperature below −25° C with an at least equimolar amount of a compound of the formula

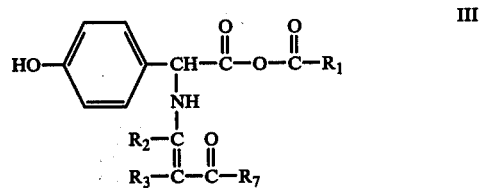

wherein $R_1$ and $R_7$ are lower alkoxy, $R_2$ is lower alkyl and $R_3$ is selected from the group consisting of lower alkyl and hydrogen previously prepared from the corresponding Dane salt and an acid chloride under anhydrous conditions in the presence of a tertiary amine in an inert, water-insoluble organic solvent.

8 Claims, No Drawings

6-(D-α-AMINO-P-HYDROXY-PHENYLACETAMIDO)-PENICILLANIC ACID PREPARATION

STATE OF THE ART

British Pat. No. 1,241,844 describes amoxicillin as being one of the more attractive semi-synthetic penicillins as it is active against a large number of gram-positive and gram-negative microorganisms.

A process is generally known from British Pat. No. 1,339,605 for the production of D-α-amino-p-hydroxybenzylpenicillin but according to Examples 1 to 5 thereof only in economically non-interesting yields (Example 1: 43% with a purity of 80%, Example 3: 20% with a purity of 16%, Example 4: 37% with a purity of 93%, while Examples 2 and 5 only just show the presence of the above-mentioned compounds).

Therefore, it was less attractive for the experts to develop the method described in the said British patent than to find alternative acylating methods and to provide a new and improved method for the preparation of the desired compound with an economically attractive yield and a relatively high purity. An additional requirement for the preparation method on a technical scale is, moreover, that the unavoidably occuring impurities are removable in a cheap and simple manner to reach the levels of purity dictated by governments.

It is known from the literature to prepare penicillanic acid and cephalosporanic acid derivatives by acylating 6-APA or 7-AC(D)A and their derivatives with the hydrochloride of 2-phenylglycine-chloride and derivatives thereof having a substituted phenyl group, whereby the said acid chloride is obtained by reacting the substituted phenylglycine with reagents like phosphorus pentachloride, thionyl chloride and phosgene. Although improved processes for the preparation of D-(−)-2-(p-hydroxyphenyl)-glycyl-chloride hydrochloride and the crystalline hemidioxane solvate thereof are known from Dutch patent application Ser. No. 73 17715 (pages 10 to 15 and Examples 16 to 23) and British Pat. No. 1,466,637, the acylation of 6-APA with the abovementioned acylating agent did hitherto not lead to results aimed by the indicated object mainly because the amoxicillin formed was so impure that further recovery to a product of the required quality hardly appeared to be possible, or the starting D-2-(p-hydroxyphenyl)-glycyl chloride hydrochloride of the required quality (purity) are only available for economically unattractive prices, if at all available.

The occurring impurities found, if an acid chloride hydrochloride in economically necessary amounts for acceptable prices is used, appear to be in agreement with the indications about the accompanying impurities in the final products and the low yields of the rather similar acylation of the said D-(−)-2-(p-hydroxyphenyl)-glycyl chloride hydrochloride of 7-aminocephalosporanic acid derivatives of Dutch patent application Ser. No. 73, 17715 (viz. Example 2, especially page 26 lines 1 and 2; Example 5; Example 10, especially page 41 line 1 and page 40 lines 20 to 30; and the Example 9 referring to further purification of the desired product). German patent application Ser. No. 2520647 discloses in this connection on page 2, lines 10 to 20 also that the application of generally used acylating agents such as acid halides in the amoxicillin synthesis is not considered.

In addition, in the preparation of D-(−)-2-(p-hydroxyphenyl)-glycyl chloride hydrochloride according to the Dutch patent application Ser. No. 73 17715 and British Pat. No. 1,466,637, phosgene is used in a relatively difficultly manageable process in which a solid is reacted with a gas. Such a process is extremely expensive in a number of countries with very stringent safety regulations, if at all possible. For the same reason, the process described in British Pat. No. 1,268,536 disclosing the preparation of 6-isocyanatopenicillanic acid from 6-APA esters with phosgene and its subsequent reaction into penicillins will not be considered for the preparation of amoxicillin.

On the other hand, German patent application Ser. No. 2,520,647, for example, discloses a process for the preparation of — inter alia — amoxicillin, in which (i) 6-APA is contacted with an excess of a strong tertiary amine base such as triethylamine in an inert, water-insoluble organic solvent such as methylene chloride or chloroform resulting in a solution of a salt of 6-APA with the base in said solvent, (ii) the remaining strong tertiary amine base is neutralized in the solvent, such as by addition of N,N-dimethylacetamide hydrochloride.

(iii) the obtained neutralized solution is contacted with a solution of a mixed acid anhydride of a short chain alkoxyformic acid and an N-protected derivative of D-2-amino-p-hydroxyphenylacetic acid, in which the N-protecting group is acid labile in a water-insoluble, inert organic solvent at a temperature of −50° C. to +30° C., preferably −30° C. to 0° C. resulting in a solution of an N-protected amixocillin derivative, (iv) the thus obtained solution is contacted with water and a strong acid such as hydrochloric acid or p-toluenesulphonic acid at room temperature or cooled to such as 0° C. to remove the acid labile N-protecting group and (v) the thus obtained amoxicillin is isolated from the thus obtained aqueous system.

Less attractive features of this process are that the process is carried out at low concentrations, that solvents become mixed so that recovery thereof becomes more difficult, that, when adding the dimethylacetamide hydrochloride, due to local high concentrations, 6-APA sometimes crystallizes, so that a very exact dosage is required.

Furthermore, a number of patent applications and patents disclose preparation methods of amoxicillin by acylating 6-APA with mixed anhydrides derived from modified Dane salts of D-2-amino-(p-hydroxyphenyl)-acetic acid, such as those described in Dutch patent application Ser. No. 64 01976 and No. 70 05611 (now Dutch Pat. No. 142,416) and British Pat. Nos. 1,327,270 and 1,347,979. However, the yields resulting from the use of Dane salts appeared to be unsatisfactory as well for the purpose of the present invention, and moreover, the Dane salts appeared to be available in economically unattractive quantities, if at all available.

Dutch patent application Ser. No. 64 01841 further discloses the protection of the carboxylic group of 6-APA by reacting it with dihalosilane derivatives and those bi-functional silicon compounds are easier accessible than the monofunctional trialkylhalogensilanes and the application thereof should, in a number of cases, lead to better yields appearing, such as from British Pat. No. 1,266,544 disclosing the preparation of intermediate organosilane penicillins by reaction of 6-APA and those bi-functional silicon compounds. The organosilane derivatives are acylated into ampicillin for example, so that an expert from the contents of this patent would expect that the use of the organosilane penicillins described therein would lead to interesting yields in the preparation of amoxicillin. However, this expectation could surprisingly not be confirmed by experiments.

Further patent literature relating to the preparation of closely related cephalosporanic acid derivatives lead to economically unattractive processes only. Dutch patent application Ser. No. 73 17715, for example, particularly Examples 2,3,5,10 and 13, does not show the slightest indication of an acylation of 7-amino-3-(1,2,3-triazol-5-yl)-thiomethyl-3-cefem-4-carboxylic acid, previously reacted with trimethylchlorosilane, with D-(−)-α-amino-α-(p-hydroxyphenyl)-acetylchloride hydrochloride and ethoxycarbonyl D-α-(1-carbomethoxy-propen-2-yl)-amino-p-hydroxyphenylacetate, respectively, in economically attractive yields, whereas particularly Examples 10 and 13 indicate very in attractive yields (viz. such as page 41, line 1, in connection with page 40 lines 20 and 26). The same may be concluded from U.S. Pat. No. 3,946,003, Example 1 (column 11 line 65) and Example 3 (column 12 line 62) and U.S. patent application Ser. No. B 516,047, Example 1 (column 7 line 44) and Example 5A (line 52).

From later patent applications such as British Pat. Nos. 1,356,737, 1,404,846 and 1,459,999, it is known to employ trivalent phosphorus derivatives instead of the above-mentioned silicon derivatives. Disadvantages of those derivatives are certainly the cost prices being 10 to 20 times higher and the toxicity and spontaneous inflamability of the di(lower alkyl) phosphorus derivatives as indicated in Inorganic Synthesis 15 (1974) pages 191 to 193.

Although it is further known from a number of patent applications such as Japanese Patent application No. 49-014687 and No. 49-048892, British Pat. Nos. 1,367,342 and 1,382,255 and German patent applications Ser. Nos. 2,460,649 and 2,621,618, to prepare amoxicillin from 6-APA and p-hydroxy-phenylglycine or lower alkyl esters thereof by enzymatic acylation, the processes of this type are also unsatisfactory for the deemed purpose in view of the yields obtained and/or the presence of the acylating enzyme in the amoxicillin-containing solution obtained.

OBJECTS OF THE INVENTION

It is an object of the invention to provide an improved process for the preparation of amoxicillin with higher yields and reduced impurity problems.

This and other objects and advantages of the invention will become obvious from the following detailed description.

THE INVENTION

The novel process of the invention for the preparation of amoxicillin comprises reacting 6-aminopenicillanic acid with at least two equivalents of a silylating agent producing trimethylsilyl groups in an anhydrous inert, water-insoluble organic solvent and reacting the resulting product at a temperature below −25° C. with an at least equimolar amount of a compound of the formula

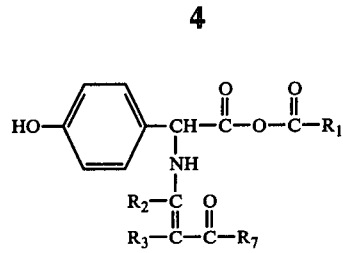

wherein $R_1$ and $R_7$ are lower alkoxy, $R_2$ is lower alkyl and $R_3$ is selected from the group consisting of lower alkyl and hydrogen previously prepared from the corresponding Dane salt and an acid chloride under anhydrous conditions in the presence of a tertiary amine in an inert, water-insoluble organic solvent.

Examples of suitable tertiary amines for use in preparing the acylating agent are N-methyl morpholine and N,N-dimethyl-benzylamine. The acylation reaction is preferably effected over 15 minutes to 2 hours. After the reaction is completed, the reaction mixture is poured into water while maintaining the pH below 2.5, preferably 0.8 to 1.2.

The products resulting from the silylation step have the formula

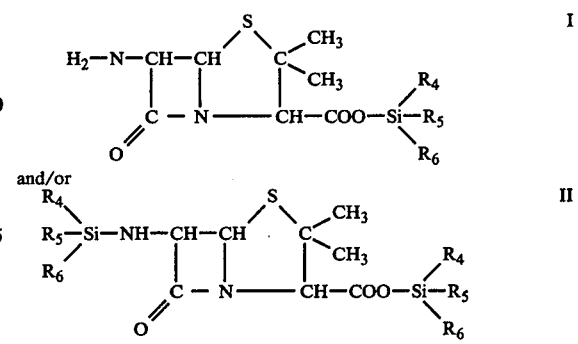

wherein $R_4$, $R_5$ and $R_6$ are individually selected from the group consisting of lower alkyl, aryllower alkyl, cycloalkyl and phenyl.

In the compounds of formula III, $R_1$ and $R_7$ are preferably methoxy, $R_2$ is preferably methyl and $R_3$ is preferably methyl or hydrogen. The term "lower" is intended to include 1 to 3 carbon atoms.

The dry, inert, water-insoluble solvent for the silylating reaction is preferably dry methylene chloride, and the silylating agent is preferably trimethylchlorosilane (TMCS) in the presence of a tertiary amine. Good results may also be obtained with trimethylsilylacetamide, bis(trimethylsilyl) acetamide and bis-trimethylsilylurea.

It has been found that the way in which the silylation is carried out is very important for the eventual yield, and the silylation is preferably carried out in dry methylene chloride containing 2 equivalents of a tertiary amine such as triethylamine and an amount of TMCS (about 2 equivalents) being such that the signal eventually recorded by a pH electrode is kept at a constant value of, for example, a pH scale value between 5.5 and 6.8 of a Radiometer pH meter type TTT2,C and a Radiometer GK 2401C electrode of an Ingold, so-called cold electrode, at a temperature between 15° to 25° C. Therefore, disilylation is preferably carried out with practically balanced mutual amounts of tri(lower alkyl)-halosilane, such as TMCS, and tertiary amine (such as TEA), and normally a very small excess of TMCS.

The dry, water-insoluble solvent used for the preparation of the so-called Dane anhydride may be dry methylene chloride to which dimethylformamide, sulfolane, tetrahydrofuran, N-methylpyrrolidone, 1,4-dioxane, acetonitrile, dimethylacetamide or tetramethylurea or a mixture thereof is added as a cosolvent to at most 25% by volume, or methylisobutylketone, to which one or more of the cosolvents mentioned above optionally may be added.

Preferably, potassium or sodium D-α-(1-carbomethoxy-propen-2-yl) amino-p-hydroxyphenylacetate is reacted with, preferably, methyl chloroformate, in contrast with the opinions hitherto held as true as may be seen from Houben-Weyl, Methoden der Organischen Chemie, 4th Edition (1974) Volume XV/2, Synthese von Peptiden, Part II, page 172. N-methylmorpholine is preferably used as a catalyst. The acid chloride is preferably added to the starting Dane salt, while the reaction is preferably carried out at a temperature of $-10°$ C. or lower, preferably at a temperature between $-10°$ C. and $-35°$ C. Mixtures of methylene chloride and the indicated cosolvents with up to about 10% by volume of cosolvent in the starting mixture are proposed as the optimal solvents for the preparation of the Dane mixed anhydride. Preferably, the concentrations of the cosolvent are selected so as to avoid mixing of solvents.

According to a further preferred process, the solution of the anhydride as prepared is cooled to a temperature of $-30°$ C. or lower and a cooled solution of silylated 6-APA is added rapidly with stirring as well as possible so that a temperature of $-50°$ C. to $-30°$ C. is reached, whereafter the reaction mixture is stirred for a further 0.5 to 2 hours. A small excess of the formula III compound is preferably employed. Then, the reaction mixture is mixed with a diluted solution of an inorganic acid such as a diluted (aqueous) hydrochloric acid solution, preferably in such a manner that the temperature becomes $-5°$ C. to $0°$ C. and the pH-value becomes $1.1 \pm 0.1$. The mixture is stirred for a further 0.5 to 2 hours at the same temperature.

After separation of the layers, the aqueous layer containing the desired compound as its hydrochloride is washed with an inert, water-insoluble organic solvent, such as methyl isobutyl-ketone or methylene chloride. The organic layer is washed with water and the wash-waters are extracted with the organic phase. Then the washing is added to the washed aqueous layer. The aqueous layer is kept at a temperature of 0° C. or lower, and by crystallization the amoxicillin is recovered by the usual method.

It is an evident advantage of the process of the invention that the concentration of the starting and final materials are relatively high, and that the use of a large excess of additional chemicals is avoided. The desired final product is prepared in a high yield and, in addition, may directly — that is to say without the hitherto usual purification steps — be brought to the required high degree of purity with lower losses and thus in a cheaper way. Moreover, mixing of solvents does not occur in the present process so that recovery is simple and economically advantageous while the starting solvent system is easily dried. The chance of unexpected crystallization of 6-APA is practically nil.

In the following examples, there are described several preferred embodiments to illustrate the invention. However, it is to be understood that the invention is not intended to be limited to the specific embodiments.

EXAMPLE 1

STEP A: Preparation of methoxycarbonyl D-α-(1-carbomethoxypropen-2-yl)-amino-p-hydroxyphenylacetate 58 g potassium D-α-(1-carbomethoxypropen-2-yl)-amino-p-hydroxyphenylacetate were weighed into 2 l reaction vessel and 200 ml of previously dried methylene chloride with a molecular sieve A4 were added. After cooling the mixture to $-40°$ C. with stirring, 25 ml of tetramethylurea were added causing the temperature to rise to about $-35°$ C. Then 0.5 ml of N-methylmorpholine and 16 ml of methyl chloroformate were added thereto. The temperature rose to about $-30°$ C. and the reaction mixture was stirred for 2 hours at $-30°$ C. at a pH-value of about 4. The reaction mixture was cooled to $-40°$ C.

STEP B: Silylation of 6-APA 35 g of 6-aminopenicillanic acid were weighed into a 1 l reaction vessel and 350 ml of methylene chloride were added thereto. With stirring, 45 ml of triethylamine were added at room temperature and then 38 ml of trimethylchlorosilane (TMSC) were added over about 10 minutes while keeping the temperature at 20° to 25° C. by cooling. After stirring for 1 hour at that temperature, the pH was about 7.5. By addition of 4 ml of TMCS, the deflection on the scale of a Radiometer pH meter type TTT2,C connected to a Radiometer GK 2401C electrode was brought to pH $6 \pm 0.2$.

STEP C: Preparation of 6-(D-α-amino-p-hydroxyphenylacetamido)-penicillanic acid The reaction mixture obtained in Step B was cooled to $-40°$ C. and was added all at once to the solution of the mixed anhydride causing the temperature to become $-30°$ C. The reaction mixture was stirred at $-30°$ C. to $-25°$ C. for 1 hour and was added to 800 ml of water whereby the temperature became 0° C. and the pH became 2.5 to 3. The pH of the mixture was adjusted to 1.1 to 1.2 by addition of 18 ml of concentrated hydrochloric acid and after stirring at 0° C. for 80 minutes, the hydrolysis was complete.

The layers were separated and the aqueous layer was washed with 100 ml of methylene chloride. The organic layer was washed with 50 ml of distilled water and after extraction of the wash water with wash-methylene chloride, the wash water was added to the aqueous layer. The coupling yield was about 92% estimated on a sample. The aqueous layer was rapidly cooled to 0° C. By crystallization, the desired compound was obtained which, after filtration, was washed with 100 ml of 50% acetone-water and 100 ml of acetone and was dried in vacuo at about 30° C. to obtain about 55.5 g of amoxicillin trihydrate (82% of theoretical yield). The remaining mother liquor contains another about 10% of amoxicillin.

EXAMPLE II

Using the same process as indicated in Example 1, except that 20 ml of dimethylacetamide were used instead of 25 ml of tetramethylurea, a coupling yield of 92% was obtained too with 55.5 g of pure amoxicillin trihydrate (82% of theoretical yield).

EXAMPLE III

STEP A: Preparation of ethoxycarbonyl D-α-(1-carbomethoxypropen-2-yl)-amino-p-hydroxyphenylacetate A thoroughly stirred suspension of 12.97 g (42.8 mmoles) of potassium D-α-(1-carbomethoxypropen-2-yl)-amino-p-hydroxyphenylacetate in 98 ml of methylisobutylketone (distilled over $K_2CO_3$) and 33 ml of tetrahydrofuran distilled over Redal, was cooled to −10° C. under an atmosphere of dry nitrogen. Then, 0.05 ml (5 drops from a Pasteur pippette) of N-methylmorpholine were added followed by a solution of 4.2 ml (44 mmoles) of ethyl formate, previously distilled and drawn under nitrogen, in 15 ml of methylisobutylketone. The reaction mixture was stirred at the same temperature for 30 minutes and the suspension was cooled to −20° C.

STEP B: Silylation of 6-APA

In a nitrogen atmosphere, 8.65 g (40 mmoles) of 6-APA were suspended in 130 ml of dry methylene chloride and 11.2 ml (80.6 mmoles) of triethylamine and 10.3 ml (82 mmoles) of trimethylchlorosilane were added subsequently. This mixture was refluxed with stirring for 1 hour and then was cooled in an ice bath to below 5° C.

STEP C: Preparation of 6-(D-α-amino-p-hydroxyphenylacetamido)-penicillanic acid With vigorous stirring the turbid solution of the Dane anhydride prepared in Step A and cooled to −20° C. was added all at once to a cooled solution of the silylated 6-APA obtained in Step B and the mixture was stirred for a further 20 minutes in an ice bath. Then, the ice bath was removed but stirring was continued with introduction of nitrogen until room temperature was reached (about 45 minutes). The mixutre was poured into with cooling 75 ml of ice water, whereafter the pH, which reached a value of 2.5 to 3 was adjusted to 1 to 1.2 with concentrated hydrochloric acid as measured with an Electrofact KCL electrode or 0.5 to 0.7 with an AgCl electrode.

After 30 minutes' stirring with ice cooling, a precipitate was not formed and, with ice cooling and stirring, a solution of 10% of KOH or NaOH was slowly added dropwise until the pH remained constant at 5.2 to 5.3 (in about 1 hour). The reaction mixture was stored in a refrigerator for 20 hours and the precipitate formed was filtered off using a G3 glass filter. The product was thoroughly washed on the filter with water followed by acetone washing. The product was dried in vacuo (generated by an oil pump, about 1 mm Hg) over a siccapent for 16 to 24 hours to obtain amoxicillin trihydrate in a yield of 71.2% with a mercurometrically measured purity of 98.4% and a biologically measured quality of 96.9%.

EXAMPLE IV

In substantially the same manner as described in Example III, amoxicillin trihydrate was obtained in a yield of 75.6% with a mercurometrically measured purity of 98.3%, a biologically measured quality of 96% and an optical rotation $[\alpha]_{20}^D$ of +302°, starting from 42.8 mmoles of potassium D-α-(1-carboethoxypropen-2-yl)-amino-p-hydroxyphenylacetate in 98 ml of methylisobutylketone and 33 ml of tetrahydrofuran, 0.05 ml of N-methylmorpholine, 44 mmoles of tetrachloroformate in 15 ml of methylisobutylketone, 40 mmoles of 6-APA in 130 ml of dry methylene chloride, 80.6 mmoles of triethylamine and 82 mmoles of trimethylchlorosilane.

EXAMPLE V

In substantially the same manner as described in Example III, amoxicillin trihydrate was obtained in a yield of 83.5% having a purity of 96% according to hydroxylamine measurement, a biologically measured quality of 94.4% and an otpical rotation $[\alpha]_{20}^D$ of 294°, starting from 45.6 mmoles of potassium D-α-(1-carbomethoxypropen-2-yl)-amino-p-hydroxyphenylacetate in 98 ml of methylisobutylketone and 33 ml of tetrahydrofuran, 0.05 ml of N-methylmorpholine, 46.8 mmoles of methyl chloroformate (purity 97%) in 15 ml of methylisobutylketone, 40 mmoles of 6-APA in 130 ml of dry methylene chloride, 80.6 mmoles of triethylamine and 82 mmoles of trimethylchlorosilane. The pH value measured with a Radiometer pH meter TTT2,C and a Radiometer GK 2401C electrode was kept constant at 6.4.

EXAMPLE VI

In substantially the same manner as described in Example III, amoxicillin trihydrate was obtained in a yield of 79.3% having a purity of 97.6% according to hydroxylamine measurement, a biologically measured quality of 95.4% and an optical rotation $[\alpha]_{20}^D$ of +300°, starting from 45.6 mmoles of potassium D-α-(1-carbomethoxypropen-2-yl)-amino-p-hydroxy phenylacetate in 110 ml of methyl isobutylketone and 10 ml of N-methypyrrolidone, 0.05 ml of N-methylmorpholine, 46.8 mmoles of methyl chloroformate (purity of 97%) in 15 ml of methylisobutylketone, 40 mmoles of 6-APA in 130 ml of dry methylene chloroform, 80.6 mmoles of triethylamine and 82 mmoles of trimethylchlorosilane. The pH value measured with a Radiometer pH meter type TTT2,C and a Radiometer GK 2401C electrode was kept constant at 6.7.

EXAMPLE VII

In substantially the same manner as described in Example III, amoxicillin trihydrate was obtained in a yield of 75% having a mercurometrically measured purity of 97.5% and a biologically meausred quality of 96.5%, starting from 42.8 mmoles of sodium D-α-(1-carbomethoxypropen-2-yl)-amino-p-hydroxyphenylacetate in 195 ml of methylisobutylketone and 65 ml of tetrahydrofuran, 0.05 ml of N-methylmorpholine, 44 mmoles of ethyl chloroformate in 30 ml of methyl isobutylketone, 40 mmoles of 6-APA in 260 ml of dry methylene chloride, 80.6 mmoles of triethylamine and 82 mmoles of trimethylchlorosilane.

EXAMPLE VIII

STEP A: Preparation of methoxycarbonyl D-α-(1-carbomethoxypropen-2-yl)-amino-p-hydroxyphenylacetate 58 g of potassium D-α-(1-carbomethoxypropen-2-yl)-amino-p-hydroxyphenylacetate were weighed into 2 l reaction vessel and 400 ml of dry methylisobutylketone were added thereto. After cooling with stirring to −15° C., 0.5 ml of N-methylmorpholine and 16 ml of methyl chloroformate were added. The reaction mixture was stirred at −11° C. for 1.5 hours and was then cooled to −43° C. to form methoxycarbonyl D-α-(1-carbomethoxypropen-2-yl)-amino-p-hydroxyphenylacetate.

STEP B: Silylation of 6-APA 35 g of 6-aminopenicillanic acid were weighed into a 1 l reaction vessel and 400 ml of methylene chloride were added thereto. After addition of 73 g of bis(trimethylsilyl) urea, the mixture was refluxed for about 2.5 hours and the mixture was then cooled to 20° C. The "pH" reading, on the scale of a Radiometer pH meter type TTT2,C, connected with a Radiometer GK-2401C electrode, was 6.3.

STEP C

After cooling, the mixture obtained in Step B was added as quickly as possible to the cooled solution of the mixed anhydride so that a temperature of −30° C. is reached. The reaction mixture was stirred at −30° to −25° C. for 1 hour and was added to 800 ml of water so that the temperature became 0° C. and the pH value became 2.5 to 3. The recovery was carried out in the same manner as described in Example I to obtain 48.4 g of amoxicillin trihydrate having a biologically measured quality of 96.8% (71.3% of theoretical yield). The remaining mother liquor appeared to contain a further 10% of amoxicillin.

EXAMPLE IX

In the same manner as described in Example VIII, 48.3 g of amoxicillin trihydrate having a purity of 97.7% were obtained by reaction of methoxycarbonyl D-α-(1-carbomethoxypropen-2-yl)-amino-p-hydroxyphenylacetate and 35 g of 6-aminopenicillanic acid, previously silylated with 72.5 g of bis(trimethylsilyl) acetamide instead of the bis(trimethylsilyl)urea.

The amoxicillin prepared by the described process was for example characterized by the following analysis data:

| | | |
|---|---|---|
| content measured by the hydroxylamine method (based on dry matter content) | | 99.8% |
| content measured mercurometrically (based on dry matter content) | | 98.7% |
| volatile components | | 12.6% |
| gas-chromatographically measured contents: | | |
| acetone | 15 mg/kg | |
| methylene chloride | 119.5 mg/kg | |
| methyl isobutylketone | 90 mg/kg | |
| dimethylaniline | 2 mg/kg | |
| $[\alpha]_{20}^D$ (on dry matter) | 301° | |
| pH value | 5.0 | |
| bulk density 6 taps: | 216 ml/100 g | |
| 50 taps: | 204 ml/100 g | |
| heavy metals | <100 ppm | |
| sulfate ash | <0.1% | |
| germ number | <10/g | |
| decomposition products: | penicilloinic acid | 0.4% |
| | penilloinic acid | 0.6% |
| solubility (clarity) HCl: | 0.6 EBC | |
| NH$_4$OH: | 0.5 EBC | |

Various modifications of the process of the invention may be made without departing from the spirit or scope thereof and it is to be understood that the invention is intended to be limited only as defined in the appended claims.

We claim:

1. A process for the preparation of amoxicillin comprising reacting 6-aminopenicillanic acid with at least two equivalents of a silylating agent producing trimethylsilyl groups in an anhydrous, inert, water-insoluble organic solvent and reacting the resulting product at a temperature below −25° C. with an at least equimolar amount of a compound of the formula

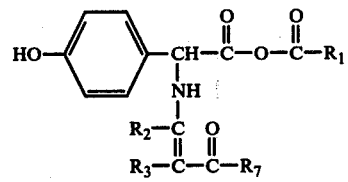

wherein $R_1$ and $R_7$ are lower alkoxy, $R_2$ is lower alkyl and $R_3$ is selected from the group consisting of lower alkyl and hydrogen previously prepared from the corresponding Dane salt and an acid chloride under anhydrous conditions in the presence of a tertiary amine in an inert, water-insoluble organic solvent.

2. The process of claim 1 wherein the tertiary amine is N-methyl-morpholine or N,N-dimethyl-benzylamine.

3. The process of claim 1 wherein the silylating reaction is carried out in dry methylene chloride with trimethylchlorosilane in the presence of a tertiary amine in mutually exactly balanced amounts.

4. The process of claim 1 wherein the dry, water-insoluble solvent for the preparation of the Dane mixed anhydride is dry methylene chloride to which a member of the group consisting of dimethylformamide, sulfolane, tetrahydrofuran, N-methylpyrrolidone, 1,4-dioxane, acetonitrile, dimethylacetamide and tetramethylurea or a mixture thereof has been added as a cosolvent, or methyl isobutylketone to which one or more of the said cosolvents optionally may be added.

5. The process of claim 4 wherein the solvent is dry methylene chloride to which a member of the group consisting of dimethylformamide, sulfolane, tetrahydrofuran, N-methylpyrrolidone, 1,4-dioxane, acetonitrile, dimethylacetamide and tetramethylurea or a mixture thereof is added.

6. The process of claim 4 wherein that the said cosolvent is added in an amount of at most 20% by volume.

7. The process of claim 1 wherein the preparation of the Dane mixed anhydride is carried out at a temperature of −10° C. to −35° C.

8. The process of claim 1 wherein sodium or potassium D-α-(1-carbomethoxypropen-2-yl)-amino-p-hydroxyphenylacetate is reacted with methyl chloroformate.

* * * * *

UNITED STATES PATENT AND TRADEMARK OFFICE
CERTIFICATE OF CORRECTION

PATENT NO. : 4,128,547

DATED : December 5, 1978

INVENTOR(S) : Johannes K. Van der Drift et al

It is certified that error appears in the above-identified patent and that said Letters Patent are hereby corrected as shown below:

On the cover sheet item (30), "52-130694" should be -- 130694/77

Column 2, line 63, "monofunctional" should be -- mono-functional --.

Column 1, line 31, "AC(D)A" should be -- A(D)CA --.

Column 8, line 1, "tetrachloroformate" should be -- methylchloroformate --.

Signed and Sealed this

Twenty-ninth Day of May 1979

[SEAL]

Attest:

RUTH C. MASON
Attesting Officer

DONALD W. BANNER
Commissioner of Patents and Trademarks